(12) United States Patent
Thullier

(10) Patent No.: US 8,507,655 B2
(45) Date of Patent: Aug. 13, 2013

(54) ANTIBODY AGAINST ANTHRAX TOXINS

(75) Inventor: Phillippe Thullier, Bernin (FR)

(73) Assignee: ETAT FRANCAIS représénté par le Délégué Général pour l'Armement, Armees (FR)

( * ) Notice: Subject to any disclaimer, the term of this patent is extended or adjusted under 35 U.S.C. 154(b) by 521 days.

(21) Appl. No.: 12/680,241

(22) PCT Filed: Sep. 26, 2008

(86) PCT No.: PCT/FR2008/051726
§ 371 (c)(1),
(2), (4) Date: Oct. 25, 2010

(87) PCT Pub. No.: WO2009/050388
PCT Pub. Date: Apr. 23, 2009

(65) Prior Publication Data
US 2011/0033450 A1     Feb. 10, 2011

(30) Foreign Application Priority Data
Sep. 26, 2007 (FR) ...................................... 07 06744

(51) Int. Cl.
*C12P 21/08* (2006.01)
(52) U.S. Cl.
USPC ...................................................... 530/387.3
(58) Field of Classification Search
None
See application file for complete search history.

(56) References Cited

U.S. PATENT DOCUMENTS
2006/0121045 A1    6/2006  Iverson et al.

FOREIGN PATENT DOCUMENTS
WO   WO 2007/084107    7/2007

OTHER PUBLICATIONS

International Search Report dated Mar. 30, 2009 for Application No. PCT/FR2008/051726.
Laffly, E. et al., "Improvement of an Antibody Neutralizing the Anthrax Toxin by Simultaneous Mutagenesis of Its Six Hypervariable Loops," J. Mol. Biol., vol. 378 (2008) pp. 1094-1103.
Laffly, E. et al., "Selection of a Macaque Fab with Framework Regions Like Those in Humans, High Affinity, and Ability to Neutralize the Protective Antigen (PA) of *Bacillus anthracis* by Binding to the Segment of PA between Residues 686 and 694," Antimicrobial Agents and Chemotherapy, vol. 49(8) (Aug. 2005) pp. 3414-3420.
Presta, L.G., "Engineering of therapeutic antibodies to minimize immunogenicity and optimize function," Advanced Drug Delivery Reviews, vol. 58 (2006) pp. 640-656.
Wark, K.L. et al., "Latest technologies for the enhancement of antibody affinity," Advanced Drug Delivery Reviews, vol. 58 (2006) pp. 657-670.
Written Opinion dated Mar. 30, 2009 for Application No. PCT/FR2008/051726.

*Primary Examiner* — Brad Duffy
(74) *Attorney, Agent, or Firm* — Frost Brown Todd LLC

(57) ABSTRACT

The invention relates to an anti PA antibody, in which the variable region of the heavy chain has an amino acid sequence represented by SEQ ID N°1 and in which the variable sequence of the light chain has an amino acid sequence represented by SEQ ID N°2, that is modified in order to improve its affinity and its tolerance in human beings.

8 Claims, 2 Drawing Sheets

Light chain

Figure 1:
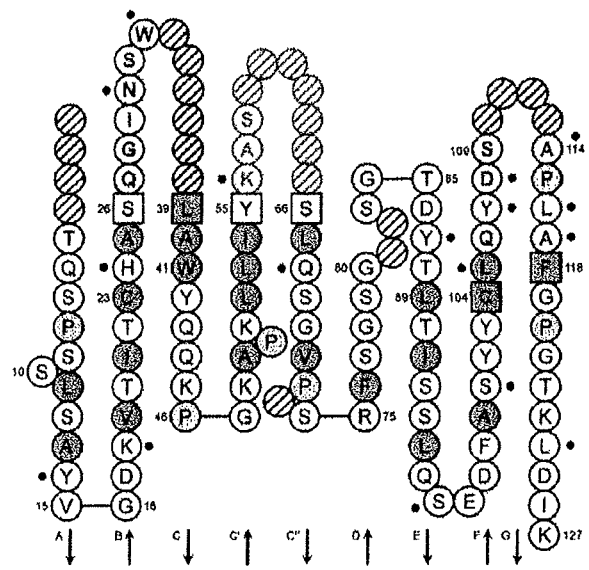
Figure 1:
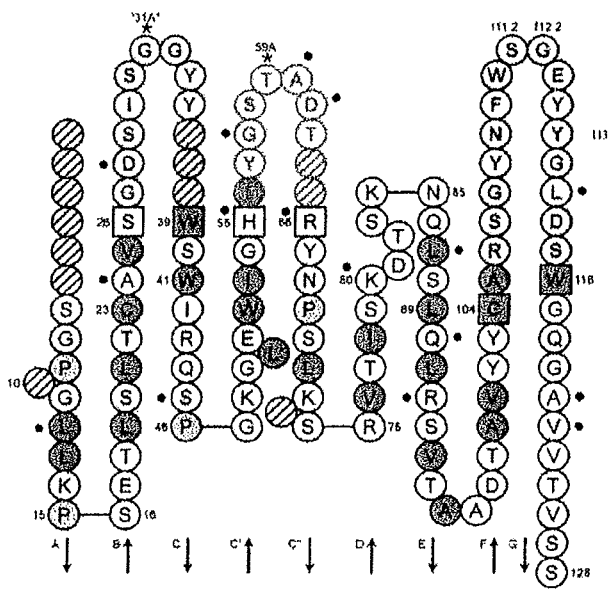

```
                                              L-CDR1                                L-CDR2
              10         20         30         40         50         60         70
35PA83   ....TQSPS SLSAVVGDRV TITCHASQGI NSW......L AWYQQKPGKA PKLLIYKAS. ......SLQS GVP.SRFSGS
6.20     .......... .......... .......... .......... .......... .......... ........L. ..........
v2       .......... .......... .......... .......... .......... .......... .......... ..........
J24.7    .......... .......... ....R..... .......... .......... .......... ........E. ..........

80         90        100   L-CDR3 110        120
35PA83   G..SGTDYTL TISSLQSEDF ASYYLQYDS ......APLAFG PGTKLDIKRA
6.20     .......... .......... .......... .......... ..........
v2       .......... .......... .......... .......... ..........
J24.7    .......... .......... .......... .......... ..........
```

Heavy chain

```
                                              H-CDR1                                H-CDR2
              10         20         30         40         50         60         70
35PA83   ......SGP .GLLKFSETL SLTCAVSGDS ISGGYY...W SWIRQSPGKG LEWIGHIYGS TADT..RYNP SLK.SRVTIS
6.20     .......... .......... .......... .......... .......... .....L.... .......... ....G....
v2       .......... .......... .......... ..S....... .......... .......... ......K.. ..R.......
J24.7    .......... .......... .......... .......... .......... .......... .......... ..........

80         90        100        H-CDR3 110       120
35PA83   KDTSKNQLSL QLRSVTAADT AVYYCARSGY NFWSGEYYGLDSWG QGAVVTVSS
6.20     .......... .......... .......... .............. .........
v2       .......... .......... .......... .............. .........
J24.7    .......... .......... .......... .............. .........
```

H-CDR3 Numbering:

```
         110   111.1  112.2  112.4
         CARSGYNF  W  S  G  E  Y  Y  GLDSWG
                       111.3  112.3
```

Fig. 2

SEQUENCE LISTING

<160> NUMBER OF SEQ ID NOS: 22

<210> SEQ ID NO 1
<211> LENGTH: 119
<212> TYPE: PRT
<213> ORGANISM: Artificial Sequence
<220> FEATURE:
<223> OTHER INFORMATION: Macaca fascicularis

<400> SEQUENCE: 1

```
Ser Gly Pro Gly Leu Leu Lys Pro Ser Glu Thr Leu Ser Leu Thr Cys
  1               5                  10                  15

Ala Val Ser Gly Asp Ser Ile Ser Gly Gly Tyr Tyr Trp Ser Trp Ile
             20                  25                  30

Arg Gln Ser Pro Gly Lys Gly Leu Glu Trp Ile Gly His Ile Tyr Gly
         35                  40                  45

Ser Thr Ala Asp Thr Arg Tyr Asn Pro Ser Leu Lys Ser Arg Val Thr
     50                  55                  60

Ile Ser Lys Asp Thr Ser Lys Asn Gln Leu Ser Leu Gln Leu Arg Ser
 65                  70                  75                  80

Val Thr Ala Ala Asp Thr Ala Val Tyr Tyr Cys Ala Arg Ser Gly Tyr
                 85                  90                  95

Asn Phe Trp Ser Gly Tyr Tyr Gly Leu Asp Ser Trp Gly Gln Gly
            100                 105                 110

Ala Val Val Thr Val Ser Ser
        115
```

<210> SEQ ID NO 2
<211> LENGTH: 103
<212> TYPE: PRT
<213> ORGANISM: Artificial Sequence
<220> FEATURE:
<223> OTHER INFORMATION: Macaca fascicularis

<400> SEQUENCE: 2

```
Thr Gln Ser Pro Ser Ser Leu Ser Ala Tyr Val Gly Asp Lys Val Thr
  1               5                  10                  15

Ile Thr Cys His Ala Ser Gln Gly Ile Asn Ser Trp Leu Ala Trp Tyr
             20                  25                  30

Gln Gln Lys Pro Gly Lys Ala Pro Lys Leu Leu Ile Tyr Lys Ala Ser
         35                  40                  45

Ser Leu Gln Ser Gly Val Pro Ser Arg Phe Ser Gly Ser Gly Ser Gly
     50                  55                  60

Thr Asp Tyr Thr Leu Thr Ile Ser Ser Leu Gln Ser Glu Asp Phe Ala
 65                  70                  75                  80

Ser Tyr Tyr Cys Leu Gln Tyr Asp Ser Ala Pro Leu Ala Phe Gly Pro
                 85                  90                  95

Gly Thr Lys Leu Asp Ile Lys
            100
```

<210> SEQ ID NO 3
<211> LENGTH: 223
<212> TYPE: PRT
<213> ORGANISM: Artificial Sequence
<220> FEATURE:
<223> OTHER INFORMATION: Macaca fascicularis

<400> SEQUENCE: 3

```
Gly Pro Gly Leu Leu Lys Pro Ser Glu Thr Leu Ser Leu Thr Cys Ala
```

-continued

```
                1               5                  10                 15
            Val Ser Gly Asp Ser Ile Ser Gly Gly Tyr Tyr Trp Ser Trp Ile Arg
                            20                  25                 30

Gln Ser Pro Gly Lys Gly Leu Glu Trp Ile Gly His Ile Tyr Gly Ser
                        35                  40                  45

Thr Ala Asp Thr Arg Tyr Asn Pro Ser Leu Lys Ser Arg Val Thr Ile
                50                  55                  60

Ser Lys Asp Thr Ser Lys Asn Gln Leu Ser Leu Gln Leu Arg Ser Val
            65                  70                  75                  80

Thr Ala Ala Asp Thr Ala Val Tyr Tyr Cys Ala Arg Ser Gly Tyr Asn
                            85                  90                  95

Phe Trp Ser Gly Glu Tyr Tyr Gly Leu Asp Ser Trp Gly Gln Gly Ala
                        100                 105                 110

Val Val Thr Val Ser Ser Ala Ser Thr Lys Gly Pro Ser Val Phe Pro
                        115                 120                 125

Leu Ala Pro Ser Ser Arg Ser Thr Ser Glu Ser Thr Ala Ala Leu Gly
                        130                 135                 140

Cys Leu Val Lys Asp Tyr Phe Pro Glu Pro Val Thr Val Ser Trp Asn
            145                 150                 155                 160

Ser Gly Ser Leu Thr Ser Gly Val His Thr Phe Pro Ala Val Leu Gln
                            165                 170                 175

Ser Ser Gly Leu Tyr Ser Leu Ser Val Val Thr Val Pro Ser Ser Ser
                        180                 185                 190

Ser Leu Gly Thr Gln Thr Tyr Val Cys Asn Val Asn His Lys Pro Ser
                        195                 200                 205

Asn Thr Lys Val Asp Lys Arg Val Glu Ile Lys Thr Cys Gly Gly
                        210                 215                 220

<210> SEQ ID NO 4
<211> LENGTH: 209
<212> TYPE: PRT
<213> ORGANISM: Artificial Sequence
<220> FEATURE:
<223> OTHER INFORMATION: Macaca fascicularis

<400> SEQUENCE: 4

Thr Gln Ser Pro Ser Ser Leu Ser Ala Tyr Val Gly Asp Lys Val Thr
            1               5                  10                 15

Ile Thr Cys His Ala Ser Gln Gly Ile Asn Ser Trp Leu Ala Trp Tyr
                            20                  25                 30

Gln Gln Lys Pro Gly Lys Ala Pro Lys Leu Leu Ile Tyr Lys Ala Ser
                        35                  40                  45

Ser Leu Gln Ser Gly Val Pro Ser Arg Phe Ser Gly Ser Gly Ser Gly
                50                  55                  60

Thr Asp Tyr Thr Leu Thr Ile Ser Ser Leu Gln Ser Glu Asp Phe Ala
            65                  70                  75                  80

Ser Tyr Tyr Cys Leu Gln Tyr Asp Ser Ala Pro Leu Ala Phe Gly Pro
                            85                  90                  95

Gly Thr Lys Leu Asp Ile Lys Arg Ala Val Ala Pro Pro Ser Val Phe
                        100                 105                 110

Ile Phe Pro Pro Ser Glu Asp Gln Val Thr Gly Thr Val Ser Val
                        115                 120                 125

Val Cys Leu Leu Asn Asn Phe Tyr Pro Arg Glu Ala Ser Val Lys Trp
            130                 135                 140

Lys Val Asp Gly Ala Leu Lys Thr Gly Asn Ser Gln Glu Ser Val Thr
            145                 150                 155                 160
```

Glu Gln Asp Ser Lys Asp Asn Thr Tyr Ser Leu Ser Ser Thr Leu Thr
              165                 170                 175

Leu Ser Ser Thr Glu Tyr Gln Ser His Lys Val Tyr Ala Cys Glu Val
            180                 185                 190

Thr His Gln Gly Leu Ser Ser Pro Val Thr Lys Ser Phe Asn Arg Gly
        195                 200                 205

Glu

<210> SEQ ID NO 5
<211> LENGTH: 670
<212> TYPE: DNA
<213> ORGANISM: Artificial Sequence
<220> FEATURE:
<223> OTHER INFORMATION: Macaca fascicularis

<400> SEQUENCE: 5
cgggcccagg actgctgaag ccttcggaaa ccctgtccct cacctgcgct gtctctggtg      60
actccatcag cggtggttac tactggagct ggatccgcca gtccccaggg aaggggctgg     120
agtggattgg gcatatctat ggtagtactg cggacaccag gtacaacccc tccctcaaga     180
gtcgagtcac catttcaaaa gacacgtcca agaaccagct ctccctgcaa ctgaggtctg     240
tgaccgccgc ggacacggcc gtgtattatt gtgcgagatc gggttacaat ttttggagtg     300
gtgaatatta cggtttggat tcctggggcc aaggggccgt cgtcaccgtc tcctcagcct     360
ccaccaaggg cccatcggtc ttccccctgg cgccctcctc caggagcacc tccgagagca     420
cagcggccct gggctgcctg gtcaaggact acttccccga accgtgacc gtgtcgtgga      480
actcaggctc cctgaccagc ggcgtgcaca ccttcccggc tgtcctacag tcctcagggc     540
tctactccct cagcagcgtg gtgaccgtgc cctccagcag cttgggcacc cagacctacg     600
tctgcaacgt aaaccacaag cccagcaaca ccaaggtgga caagagagtt gagatcaaaa     660
catgtggtgg                                                           670

<210> SEQ ID NO 6
<211> LENGTH: 634
<212> TYPE: DNA
<213> ORGANISM: Artificial Sequence
<220> FEATURE:
<223> OTHER INFORMATION: Macaca fascicularis

<400> SEQUENCE: 6
acccagtctc catcgtccct gtctgcatat gtgggagaca agtcaccat cacttgccat       60
gccagtcagg gtattaacag ttggttagcc tggtatcagc agaaaccagg gaaagcccct     120
aaacttctga tctataaggc gtccagtttg caaagtgggg tcccatcaag gttcagcggc     180
agtggatctg ggacagatta ctctctcacc atcagcagct tgcagtctga agactttgct     240
tcttattact gtctacaata tgacagtgcc ccattggctt tcggccccgg gaccaagctg     300
gatatcaaac gggctgtggc tccaccatct gtcttcatct tcccgccatc tgaagatcag     360
gtgcatctg gaactgtctc tgttgtgtgc ctgctgaata acttctatcc cagagaggcc      420
agcgtaaagt ggaaggtgga tggtgccctc aaaacgggta actcccagga gagtgtcaca     480
gagcaggaca gcaaggacaa cacctacagc ctgagcagca ccctgacgct gagcagcaca     540
gagtaccaga gtcacaaagt ctatgcctgc gaagtcaccc atcagggcct gagttcgccc     600
gtcacaaaga gcttcaacag gggagagtgt taat                                634

<210> SEQ ID NO 7

<211> LENGTH: 125
<212> TYPE: PRT
<213> ORGANISM: Artificial Sequence
<220> FEATURE:
<223> OTHER INFORMATION: VH V2 variant

<400> SEQUENCE: 7

```
Gln Val Gln Leu Gln Glu Ser Gly Pro Gly Leu Leu Lys Pro Ser Glu
 1               5                  10                  15

Thr Leu Ser Leu Thr Cys Ala Val Ser Gly Asp Ser Ile Ser Ser Gly
            20                  25                  30

Tyr Tyr Trp Ser Trp Ile Arg Gln Ser Pro Gly Lys Gly Leu Glu Trp
        35                  40                  45

Ile Gly His Ile Tyr Gly Ser Thr Ala Asp Thr Lys Tyr Asn Pro Ser
 50                  55                  60

Leu Arg Ser Arg Val Thr Ile Ser Lys Asp Thr Ser Lys Asn Gln Leu
 65                  70                  75                  80

Ser Leu Gln Leu Arg Ser Val Thr Ala Ala Asp Thr Ala Val Tyr Tyr
                85                  90                  95

Cys Ala Arg Ser Gly Tyr Asn Phe Trp Ser Gly Glu Tyr Tyr Gly Leu
            100                 105                 110

Asp Ser Trp Gly Gln Gly Ala Val Val Thr Val Ser Ser
        115                 120                 125
```

<210> SEQ ID NO 8
<211> LENGTH: 107
<212> TYPE: PRT
<213> ORGANISM: Artificial Sequence
<220> FEATURE:
<223> OTHER INFORMATION: VL V2 variant

<400> SEQUENCE: 8

```
Ala Ile Gln Leu Thr Gln Ser Pro Ser Ser Leu Ser Ala Tyr Val Gly
 1               5                  10                  15

Asp Lys Val Thr Ile Thr Cys His Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
 50                  55                  60

Ser Gly Ser Gly Thr Asp Tyr Thr Leu Thr Ile Ser Ser Leu Gln Ser
 65                  70                  75                  80

Glu Asp Phe Ala Ser Tyr Tyr Cys Leu Gln Tyr Asp Ser Ala Pro Leu
                85                  90                  95

Ala Phe Gly Pro Gly Thr Lys Leu Asp Ile Lys
            100                 105
```

<210> SEQ ID NO 9
<211> LENGTH: 125
<212> TYPE: PRT
<213> ORGANISM: Artificial Sequence
<220> FEATURE:
<223> OTHER INFORMATION: VH 6.20 variant

<400> SEQUENCE: 9

```
Gln Val Gln Leu Gln Glu Ser Gly Pro Gly Leu Leu Lys Pro Ser Glu
 1               5                  10                  15

Thr Leu Ser Leu Thr Cys Ala Val Ser Gly Asp Ser Ile Ser Gly Gly
            20                  25                  30

Tyr Tyr Trp Ser Trp Ile Arg Gln Ser Pro Gly Lys Gly Leu Glu Trp
```

```
                 35                  40                  45
Ile Gly Leu Ile Tyr Gly Ser Thr Ala Asp Thr Arg Tyr Asn Pro Ser
 50                  55                  60

Leu Lys Gly Arg Val Thr Ile Ser Lys Asp Thr Ser Lys Asn Gln Leu
 65                  70                  75                  80

Ser Leu Gln Leu Arg Ser Val Thr Ala Ala Asp Thr Ala Val Tyr Tyr
                 85                  90                  95

Cys Ala Arg Ser Gly Tyr Asn Phe Trp Ser Gly Glu Tyr Tyr Gly Leu
                100                 105                 110

Asp Ser Trp Gly Gln Gly Ala Val Val Thr Val Ser Ser
                115                 120                 125

<210> SEQ ID NO 10
<211> LENGTH: 107
<212> TYPE: PRT
<213> ORGANISM: Artificial Sequence
<220> FEATURE:
<223> OTHER INFORMATION: VL 6.20 variant

<400> SEQUENCE: 10

Ala Ile Gln Leu Thr Gln Ser Pro Ser Ser Leu Ser Ala Tyr Val Gly
  1               5                  10                  15

Asp Lys Val Thr Ile Thr Cys His Ala Ser Gln Gly Ile Asn Ser Trp
                 20                  25                  30

Leu Ala Trp Tyr Gln Gln Lys Pro Gly Lys Ala Pro Lys Leu Leu Ile
                 35                  40                  45

Tyr Lys Ala Ser Ser Leu Leu Ser Gly Val Pro Ser Arg Phe Ser Gly
 50                  55                  60

Ser Gly Ser Gly Thr Asp Tyr Thr Leu Thr Ile Ser Ser Leu Gln Ser
 65                  70                  75                  80

Glu Asp Phe Ala Ser Tyr Tyr Cys Leu Gln Tyr Asp Ser Ala Pro Leu
                 85                  90                  95

Ala Phe Gly Pro Gly Thr Lys Leu Asp Ile Lys
                100                 105

<210> SEQ ID NO 11
<211> LENGTH: 125
<212> TYPE: PRT
<213> ORGANISM: Artificial Sequence
<220> FEATURE:
<223> OTHER INFORMATION: VH J24.15 variant

<400> SEQUENCE: 11

Gln Val Gln Leu Gln Glu Ser Gly Pro Gly Leu Leu Lys Pro Ser Glu
  1               5                  10                  15

Thr Leu Ser Leu Thr Cys Ala Val Ser Gly Asp Ser Ile Ser Gly Gly
                 20                  25                  30

Tyr Tyr Trp Ser Trp Ile Arg Gln Ser Pro Gly Lys Gly Leu Glu Trp
                 35                  40                  45

Ile Gly His Ile Tyr Gly Ser Thr Ala Asp Thr Arg Tyr Asn Pro Ser
 50                  55                  60

Leu Lys Ser Arg Val Thr Ile Ser Lys Asp Thr Ser Lys Asn Gln Leu
 65                  70                  75                  80

Ser Leu Gln Leu Arg Ser Val Thr Ala Ala Asp Thr Ala Val Tyr Tyr
                 85                  90                  95

Cys Ala Arg Ser Gly Tyr Asn Phe Trp Ser Gly Glu Tyr Tyr Gly Leu
                100                 105                 110

Asp Leu Trp Gly Gln Gly Ala Val Val Thr Val Ser Ser
```

```
            115                 120                 125

<210> SEQ ID NO 12
<211> LENGTH: 107
<212> TYPE: PRT
<213> ORGANISM: Artificial Sequence
<220> FEATURE:
<223> OTHER INFORMATION: VL J24.15 variant

<400> SEQUENCE: 12

Ala Ile Gln Leu Thr Gln Ser Pro Ser Ser Leu Ser Ala Tyr Val Gly
 1               5                  10                  15

Asp Lys Val Thr Ile Thr Cys His Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Arg Ser Leu Gln Ser Gly Val Pro Ser Arg Phe Ser Gly
 50                  55                  60

Ser Gly Ser Gly Thr Asp Tyr Thr Leu Thr Ile Ser Ser Leu Gln Ser
 65                  70                  75                  80

Glu Asp Phe Ala Ser Tyr Tyr Cys Leu Gln Tyr Asp Ser Ala Pro Leu
                85                  90                  95

Ala Phe Gly Pro Gly Thr Lys Leu Asp Ile Lys
            100                 105

<210> SEQ ID NO 13
<211> LENGTH: 125
<212> TYPE: PRT
<213> ORGANISM: Artificial Sequence
<220> FEATURE:
<223> OTHER INFORMATION: VH J24.7 variant

<400> SEQUENCE: 13

Gln Val Gln Leu Gln Glu Ser Gly Pro Gly Leu Leu Lys Pro Ser Glu
 1               5                  10                  15

Thr Leu Ser Leu Thr Cys Ala Val Ser Gly Asp Ser Ile Ser Gly Gly
            20                  25                  30

Tyr Tyr Trp Ser Trp Ile Arg Gln Ser Pro Gly Lys Gly Leu Glu Trp
        35                  40                  45

Ile Gly His Ile Tyr Gly Ser Thr Ala Asp Thr Arg Tyr Asn Pro Ser
 50                  55                  60

Leu Lys Ser Arg Val Thr Ile Ser Lys Asp Thr Ser Lys Asn Gln Leu
 65                  70                  75                  80

Ser Leu Gln Leu Arg Ser Val Thr Ala Ala Asp Thr Ala Val Tyr Tyr
                85                  90                  95

Cys Ala Arg Ser Gly Tyr Asn Phe Trp Ser Gly Glu Tyr Tyr Gly Leu
            100                 105                 110

Asp Ser Trp Gly Gln Gly Ala Val Val Thr Val Ser Ser
        115                 120                 125

<210> SEQ ID NO 14
<211> LENGTH: 107
<212> TYPE: PRT
<213> ORGANISM: Artificial Sequence
<220> FEATURE:
<223> OTHER INFORMATION: VL J24.15 variant

<400> SEQUENCE: 14

Ala Ile Gln Leu Thr Gln Ser Pro Ser Ser Leu Ser Ala Tyr Val Gly
 1               5                  10                  15
```

-continued

Asp Lys Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Gln Glu Gly Val Pro Ser Arg Phe Ser Gly
50                  55                  60

Ser Gly Ser Gly Thr Asp Tyr Thr Leu Thr Ile Ser Ser Leu Gln Ser
65                  70                  75                  80

Glu Asp Phe Ala Ser Tyr Tyr Cys Leu Gln Tyr Asp Ser Ala Pro Leu
                85                  90                  95

Ala Phe Gly Pro Gly Thr Lys Leu Asp Ile Lys
                100                 105

<210> SEQ ID NO 15
<211> LENGTH: 125
<212> TYPE: PRT
<213> ORGANISM: Artificial Sequence
<220> FEATURE:
<223> OTHER INFORMATION: VH V2 variant human

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Tyr Tyr Trp Ser Trp Ile Arg Gln Pro Pro Gly Lys Gly Leu Glu Trp
            35                  40                  45

Ile Gly His Ile Tyr Gly Ser Thr Ala Asp Thr Asn Tyr Asn Pro Ser
50                  55                  60

Leu Arg Ser Arg Val Thr Ile Ser Lys Asp Thr Ser Lys Asn Gln Phe
65                  70                  75                  80

Ser Leu Gln Leu Ser Ser Val Thr Ala Ala Asp Thr Ala Val Tyr Tyr
                85                  90                  95

Cys Ala Arg Ser Gly Tyr Asn Phe Trp Ser Gly Glu Tyr Tyr Gly Leu
                100                 105                 110

Asp Ser Trp Gly Gln Gly Thr Leu Val Thr Val Ser Ser
            115                 120                 125

<210> SEQ ID NO 16
<211> LENGTH: 107
<212> TYPE: PRT
<213> ORGANISM: Artificial Sequence
<220> FEATURE:
<223> OTHER INFORMATION: VL V2 variant human

<400> SEQUENCE: 16

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Ala Pro Leu
                85                  90                  95

```
Ala Phe Gly Pro Gly Thr Lys Val Asp Ile Lys
            100                 105
```

<210> SEQ ID NO 17
<211> LENGTH: 125
<212> TYPE: PRT
<213> ORGANISM: Artificial Sequence
<220> FEATURE:
<223> OTHER INFORMATION: VH 6.20 variant human

<400> SEQUENCE: 17

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Ser Gly Gly
             20                  25                  30

Tyr Tyr Trp Ser Trp Ile Arg Gln Pro Pro Gly Lys Gly Leu Glu Trp
         35                  40                  45

Ile Gly Leu Ile Tyr Gly Ser Thr Ala Asp Thr Asn Tyr Asn Pro Ser
 50                  55                  60

Leu Lys Gly Arg Val Thr Ile Ser Lys Asp Thr Ser Lys Asn Gln Phe
 65                  70                  75                  80

Ser Leu Gln Leu Ser Ser Val Thr Ala Ala Asp Thr Ala Val Tyr Tyr
                 85                  90                  95

Cys Ala Arg Ser Gly Tyr Asn Phe Trp Ser Gly Glu Tyr Tyr Gly Leu
            100                 105                 110

Asp Ser Trp Gly Gln Gly Thr Leu Val Thr Val Ser Ser
        115                 120                 125
```

<210> SEQ ID NO 18
<211> LENGTH: 107
<212> TYPE: PRT
<213> ORGANISM: Artificial Sequence
<220> FEATURE:
<223> OTHER INFORMATION: VL 6.20 variant human

<400> SEQUENCE: 18

```
Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Asn Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Leu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Ser Ala Pro Leu
                 85                  90                  95

Ala Phe Gly Pro Gly Thr Lys Val Asp Ile Lys
            100                 105
```

<210> SEQ ID NO 19
<211> LENGTH: 125
<212> TYPE: PRT
<213> ORGANISM: Artificial Sequence
<220> FEATURE:
<223> OTHER INFORMATION: VH J24.15 variant human

<400> SEQUENCE: 19

```
Gln Val Gln Leu Gln Glu Ser Gly Pro Gly Leu Val Lys Pro Ser Glu
  1               5                  10                  15
```

```
Thr Leu Ser Leu Thr Cys Thr Val Ser Gly Asp Ser Ile Ser Gly Gly
            20                  25                  30

Tyr Tyr Trp Ser Trp Ile Arg Gln Pro Pro Gly Lys Gly Leu Glu Trp
        35                  40                  45

Ile Gly His Ile Tyr Gly Ser Thr Ala Asp Thr Asn Tyr Asn Pro Ser
    50                  55                  60

Leu Lys Ser Arg Val Thr Ile Ser Lys Asp Thr Ser Lys Asn Gln Phe
65                  70                  75                  80

Ser Leu Gln Leu Ser Ser Val Thr Ala Ala Asp Thr Ala Val Tyr Tyr
            85                  90                  95

Cys Ala Arg Ser Gly Tyr Asn Phe Trp Ser Gly Glu Tyr Tyr Gly Leu
            100                 105                 110

Asp Leu Trp Gly Gln Gly Thr Leu Val Thr Val Ser Ser
            115                 120                 125

<210> SEQ ID NO 20
<211> LENGTH: 107
<212> TYPE: PRT
<213> ORGANISM: Artificial Sequence
<220> FEATURE:
<223> OTHER INFORMATION: VL J24.15 variant human

<400> SEQUENCE: 20

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Arg Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Ala Pro Leu
            85                  90                  95

Ala Phe Gly Pro Gly Thr Lys Val Asp Ile Lys
            100                 105

<210> SEQ ID NO 21
<211> LENGTH: 125
<212> TYPE: PRT
<213> ORGANISM: Artificial Sequence
<220> FEATURE:
<223> OTHER INFORMATION: VH J24.7 variant human

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Gly Gly
            20                  25                  30

Tyr Tyr Trp Ser Trp Ile Arg Gln Pro Pro Gly Lys Gly Leu Glu Trp
        35                  40                  45

Ile Gly His Ile Tyr Gly Ser Thr Ala Asp Thr Asn Tyr Asn Pro Ser
    50                  55                  60

Leu Lys Ser Arg Val Thr Ile Ser Lys Asp Thr Ser Lys Asn Gln Phe
65                  70                  75                  80

Ser Leu Gln Leu Ser Ser Val Thr Ala Ala Asp Thr Ala Val Tyr Tyr
            85                  90                  95
```

```
Cys Ala Arg Ser Gly Tyr Asn Phe Trp Ser Gly Glu Tyr Tyr Gly Leu
            100                 105                 110

Asp Ser Trp Gly Gln Gly Thr Leu Val Thr Val Ser Ser
        115                 120                 125

<210> SEQ ID NO 22
<211> LENGTH: 107
<212> TYPE: PRT
<213> ORGANISM: Artificial Sequence
<220> FEATURE:
<223> OTHER INFORMATION: VL J24.7 variant human

<400> SEQUENCE: 22

Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Asn Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Gln Glu Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Ser Ala Pro Leu
                 85                  90                  95

Ala Phe Gly Pro Gly Thr Lys Val Asp Ile Lys
                100                 105
```

ANTIBODY AGAINST ANTHRAX TOXINS

The present invention relates to antibodies against anthrax toxins. In particular, the present invention relates to an anti-PA antibody, directed against the PA subunit of the lethal and edematous toxins of anthrax, modified so as to present improved affinity and tolerance.

Anthrax is a disease caused by a Gram-positive bacillus, *Bacillus anthracis*. This bacterium is nonmotile and forms spores when it is put in an environment unfavorable to its survival. The spores can survive for 24 hours in the air and for about 100 years in the soil, and possess properties of resistance to heat or to disinfectants.

Infection with anthrax can take three forms: cutaneous, pulmonary or intestinal. Pulmonary infection is most often fatal. If inhaled, the spores of *B. anthracis* enter the alveoli, where they are phagocytosed notably by macrophages and dendritic cells. The spores germinate in these cells and the vegetative forms multiply in the ganglia. The bacteria then pass into the blood, reproduce continuously and produce toxins, which are partly responsible for the lethality of the disease. Anthrax toxins are composed of three separate proteins: protective antigen (PA, 83 kDa before intracellular enzymatic cleavage and 63 kDa after cleavage), lethal factor (LF, 90 kDa) and edema factor (EF, 89 kDa). The lethal toxin is formed from PA and LF; and the edematous toxin, which has a minor role in the physiology of the disease, is formed from PA and EF. These proteins are secreted by the bacterium as nontoxic monomers, and undergo assembly on the surface of the target cells, forming toxic complexes.

To date, several antibiotics, such as penicillin, doxycycline and fluoroquinones, have been used for the treatment of anthrax infections. However, some of these antibiotics might not have effects on certain, antibiotic-resistant, strains. In particular, some of these treatments might not be usable in case of terrorism or bacteriological warfare, when antibiotic-resistant strains could be spread deliberately. Moreover, as the antibiotics cannot inhibit the action of anthrax toxin, it is necessary for these antibiotics to be administered at early stages of infection, but early diagnosis is difficult to establish as the initial symptoms are nonspecific.

Vaccines with protective antigen PA as the main component have been developed but are only used for persons who are very likely to come in contact with *B. anthracis*. Moreover, as it takes several months to acquire sufficient immunity, these vaccines cannot be used in emergency situations. At present, in France, none of these vaccines has been approved for human use. It is therefore necessary to develop novel therapeutic and preventive approaches, other than antibiotics.

Passive immunization with antibodies represents an effective strategy for neutralizing the toxin. Several trials have been conducted for neutralizing the lethal anthrax toxin by means of monoclonal antibodies against the protective antigen (PA) and the lethal factor (LF). The neutralization of the lethal anthrax toxin by means of an antibody can take place by inhibition of binding between PA and its cellular receptor, inhibition of cleavage of PA, inhibition of binding between PA and LF or inhibition of the action of LF, for example.

The development of novel antibodies for neutralizing anthrax toxin is thus of general interest for the prevention and effective treatment of anthrax.

In a recent work, the inventors immunized a macaque with the protective antigen PA83 to obtain antibodies intended for treating anthrax infection in humans. Starting from bone marrow, the inventors amplified the genes coding for specific antibody fragments of PA83 and cloned them to obtain a library. A fragment that has strong affinity (Kd=3.4 nM) and is strongly neutralizing (50% inhibitory concentration=5.6+/−0.13 nM), designated 35PA83, was then isolated (Laffly et al., Antimicrobial agents and chemotherapy, 2005, 49(8): 3414-3420). The inventors demonstrated that the 35PA83 immunoglobulin fragment neutralizes anthrax toxin by preventing the interaction of PA with its cellular receptor.

The inventors then attempted to modify this immunoglobulin fragment to improve its characteristics for the purpose of medical use (prophylactic or therapeutic), by improving its affinity and its tolerance in humans. Improving the affinity of this immunoglobulin fragment offers the advantage of using a smaller amount of immunoglobulin to obtain sufficient biological activity and also makes it possible to reduce the cost of treatment. Improving the tolerance in humans offers the advantage of avoiding immune responses directed against this antibody fragment.

The present invention therefore aims to supply a modified anti-PA antibody starting from the 35PA83 immunoglobulin fragment.

The present invention also relates to a composition comprising said modified antibody as well as a pharmaceutical composition comprising said modified antibody.

The present invention also relates to the use of said modified antibody for the preparation of a pharmaceutical composition intended for the treatment or prevention of anthrax infection.

The present invention also relates to a kit for the detection of an anthrax toxin, comprising said modified antibody as well as a method of detection of an anthrax toxin.

The present invention will be better understood with the aid of the following definitions.

The term "antibody" refers to an immunoglobulin molecule or a fragment of an immunoglobulin molecule having the capacity to bind specifically to a particular antigen. Immunoglobulin fragments that are well known are for example the fragments F(ab')2, Fab, Fv, scFv and Fd.

The term "anthrax" refers to any disease caused, directly or indirectly, by infection with *Bacillus anthracis*. The initial symptoms of infection by inhalation resemble those of a cold (fever, muscular pains, etc.). After several days, these symptoms progress to severe problems of respiratory distress and septic shock. Inhalation of anthrax is generally fatal. Cutaneous infection with anthrax takes place when the bacterium enters the skin at a pre-existing break in the skin. Initially this infection gives rise to a papule, which develops in two-three days into a vesicle and then into an ulcer with a diameter of 1-3 centimeters with a necrotic area at the center. Gastrointestinal infection with anthrax develops following consumption of contaminated meat and is characterized by acute inflammation of the intestinal tract.

The term "isolated" means "amplified in vitro by PCR", "produced recombinantly by cloning", "purified by separation on gel or by cleavage", or "synthesized for example by chemical synthesis".

The term "vector" refers to a nucleic acid in which the sequence of interest can be inserted by restriction and then ligation for transport between different genetic environments or for expression in a host cell. The vectors are for example plasmids, cosmids, yeast artificial chromosomes (YAC), bacterial artificial chromosomes (BAC) and artificial chromosomes derived from bacteriophage P1 (PAC), and vectors derived from viruses. A cloning vector is a vector capable of replicating in a host cell and which is moreover characterized by the presence of one or more restriction sites for endonucleases. An expression vector is a vector in which the DNA sequence of interest can be inserted by restriction or ligation in such a way that it can be replicated and/or transcribed into RNA. The vectors can moreover contain one or more markers for selection or identification of the cells that have been transformed or transfected with the vector.

The term "humanized antibody" refers to antibodies of animal origin in which human components have been substituted for certain original components.

The term "prevention of a disease" corresponds to the prevention of the appearance of this disease in a subject, in particular a human, in whom the disease has not yet become manifest.

The term "treatment of a disease" corresponds to the inhibition of said disease, i.e. the stopping of its development, its regression, or to the disappearance of the symptoms and consequences of the disease, or to the disappearance of the causes of the disease.

The term "therapeutically effective amount" refers to the amount that is sufficient to effect the treatment when it is administered to a subject who needs said treatment. The therapeutically effective amount depends on the subject, the stage of the disease to be treated and the method of administration, and can be determined by routine procedures by a person skilled in the art.

As is well known, only a part of the antibody, the variable region, is involved in the binding of the antibody to its epitope. The constant regions of the antibody activate the immune effectors, phagocytes or killer cells, and complement; these constant regions are not involved in binding to the antigen. An antibody whose constant region (Fc) has been enzymatically cleaved so as to preserve its hinge region is designated as an F(ab')2 fragment and conserves the two binding sites to the antigen.

Similarly, an antibody whose constant region, including the hinge region, has been enzymatically cleaved, or which was produced without this region, is designated as a Fab fragment and conserves one of the two binding sites to the antigen. The Fab fragments consist of a light chain which is bound covalently to a portion of the heavy chain called Fd.

In the variable region, there are the regions that determine complementarity (CDRs, complementarity determining regions), also called hypervariable regions, which interact directly with the antigen. Modifying the CDRs may therefore make it possible to modify the affinity of an antibody. In the variable region, there are regions of a second type, called framework regions (FRs), which maintain the tertiary structure of the CDRs. These framework regions are fairly specific to the species in which the antibody was produced. In the Fd fragment of the heavy chain and in the light chain, there are four framework regions (FR1 to 4) separated respectively by three CDRs (CDR1 to 3).

The present invention relates to an anti-PA antibody in which the variable region of the heavy chain has an amino acid sequence represented by SEQ ID No. 1 and the variable region of the light chain has an amino acid sequence represented by SEQ ID No. 2, characterized in that said antibody is modified with at least one mutation in the variable region of the heavy chain or in the variable region of the light chain to display affinity greater than that of the unmodified antibody.

The peptide sequence SEQ ID No. 3, corresponding to the Fd fragment of the 35PA83 antibody, described in Laffly et al., is accessible in computer databases, such as Genbank, under number CAH17920 and the peptide sequence SEQ ID No. 4, corresponding to the light chain of the 35PA83 antibody is accessible in the same way under number CAH17921.

The variable regions of these sequences are presented in the form of a two-dimensional diagram in FIG. 1.

The DNA sequences coding for the Fd fragment and the light chain of the 35PA83 antibody, called here SEQ ID No. 5 and SEQ ID No. 6, are also accessible in computer databases, under numbers AJ810486 and AJ810487, respectively.

The affinity $K_D$ of an antibody can be measured by the conventional techniques known by a person skilled in the art.

The unmodified (i.e. not mutated) parent antibody 35PA83 has an affinity $K_D$ equal to $3.4\ 10^{-9}$. This affinity constant was calculated from the association and dissociation constants measured in real time by surface plasmon resonance, as explained in the examples.

In one embodiment of the present invention, the modified anti-PA antibody according to the invention is modified with at least one mutation selected from G/S (31A), R/K (66), K/R (73), D/G (28), G/E (31A), H/L (55), S/G (74), Y/T (113), S/L (117) in the variable region of the heavy chain, and Q/R (68), Q/R (27), A/P (114), Q/L (68), P/S (115), H/R (24), S/E (69), S/R (58) in the variable region of the light chain.

The mutation G/S (31A) in the variable region of the heavy chain means that the amino acid G in position 31A (see FIG. 1 for the positions of the amino acids) has been substituted with the amino acid S.

This anti-PA antibody, modified with at least one of the mutations mentioned above in the variable region of the heavy chain or in the variable region of the light chain, displays improved affinity for PA relative to that of the 35PA83 antibody.

The present invention therefore supplies fragments F(ab')2, Fab, Fv, scFv and Fd of a modified anti-PA antibody according to the invention, as well as chimeric antibodies in which the Fc part of the antibody comes from human or nonhuman homologous sequences.

According to one embodiment of the invention, the Fc part of the antibody can be selected so as to produce IgAs, IgMs or IgGs.

According to another embodiment of the invention, the Fc part of the antibody can be an Fc part derived from mice, horses, sheep, cattle or other mammals.

According to a preferred embodiment of the invention, the modified anti-PA antibody according to the invention possesses a part Fc of human origin. These complete antibodies are preferred for administration in humans as they have a longer half-life than the antibody fragments such as Fab, and are more suitable for intravenous, intraperitoneal, intramuscular, subcutaneous or transdermal administration.

In certain embodiments of the invention, the Fab fragments are preferred for the following reasons: a) as the Fab fragments only possess a single binding site to the antigen, immune complexes of large size cannot form, b) absence of the region Fc prevents the appearance of an inflammatory reaction activated by Fc, such as activation of the complement cascade, c) it is easier for a small Fab molecule to penetrate into the tissues, and d) Fabs can be produced easily and at low cost in bacteria such as *E. coli*.

Thus, one object of the present invention is to supply Fabs of the modified anti-PA antibody according to the invention, fragments of this antibody that are smaller or larger than the Fab fragments or alternatively epitope binding peptides, and in particular peptides derived from the hypervariable regions of the modified anti-PA antibody according to the invention.

In a first embodiment of the invention, the modified anti-PA antibody according to the invention is characterized in that said at least one mutation is selected from G/S (31A), R/K (66), K/R (73), D/G (28), G/E (31A), H/L (55), S/G (74), Y/T (113), S/L (117) in the variable region of the heavy chain.

In a second embodiment of the invention, the modified anti-PA antibody according to the invention is characterized in that said at least one mutation is selected from Q/R (68), Q/R (27), A/P (114), Q/L (68), P/S (115), H/R (24), S/E (69), S/R (58) in the variable region of the light chain.

In a third embodiment of the invention, the modified anti-PA antibody according to the invention is characterized in that it is modified with at least one mutation selected from G/S (31A), R/K (66), K/R (73), D/G (28), G/E (31A), H/L (55), S/G (74), Y/T (113), S/L (117) in the variable region of the heavy chain and at least one mutation selected from Q/R (68), Q/R (27), A/P (114), Q/L (68), P/S (115), H/R (24), S/E (69), S/R (58) in the variable region of the light chain.

According to a preferred embodiment of the invention, said modified anti-PA antibody according to the invention comprises the following three mutations in the variable region of the heavy chain:

G/S (31A)
R/K (66)
K/R (73).

According to another preferred embodiment of the invention, said modified anti-PA antibody according to the invention comprises the following two mutations in the variable region of the heavy chain:

H/L (55)
S/G (74), and the mutation Q/L (68) in the variable region of the light chain.

According to another preferred embodiment of the invention, said modified anti-PA antibody according to the invention comprises the following mutation in the variable region of the heavy chain:

S/L (117)

and the mutation S/R (58) in the variable region of the light chain.

According to another preferred embodiment of the invention, said modified anti-PA antibody according to the invention comprises the following two mutations in the variable region of the light chain:

H/R(24) and
S/E(69).

According to one embodiment of the invention, said modified PA antibody according to the invention comprises the following mutations in the variable region of the heavy chain: none/Q (1), none/V (2), none/Q (3), none/L (4), none/Q (5) and none/E (6), and the following mutations in the variable region of the light chain: none/A (1), none/I (2), none/Q (3) and none/L (4).

In this embodiment, the anti-PA antibody comprising the following three mutations in the variable region of the heavy chain: G/S (31A), R/K (66) and K/R (73) has the sequence SEQ ID NO: 7 as the variable region of the heavy chain and the sequence SEQ ID NO: 8 as the variable region of the light chain.

In this embodiment, the anti-PA antibody comprising the following two mutations in the variable region of the heavy chain: H/L (55) and S/G (74), and the mutation Q/L (68) in the variable region of the light chain has the sequence SEQ ID NO: 9 as the variable region of the heavy chain and the sequence SEQ ID NO: 10 as the variable region of the light chain.

In this embodiment, the anti-PA antibody comprising the mutation S/L (117) in the variable region of the heavy chain and the mutation S/R (58) in the variable region of the light chain has the sequence SEQ ID NO: 11 as the variable region of the heavy chain and the sequence SEQ ID NO: 12 as the variable region of the light chain.

In this embodiment, the anti-PA antibody comprising the following two mutations in the variable region of the light chain: H/R(24) and S/E(69) has the sequence SEQ ID NO: 13 as the variable region of the heavy chain and the sequence SEQ ID NO: 14 as the variable region of the light chain.

One object of the present invention is also to supply a modified anti-PA antibody having improved affinity relative to the nonmutated 35PA83 antibody as well as better tolerance by the human immune system. This humanized antibody offers the advantage that it does not induce, or induces less of an immune response against itself, and has a longer half-life.

The present invention therefore relates to a modified and humanized anti-PA antibody according to the invention, characterized in that it additionally comprises at least one mutation in the variable region of the heavy chain selected from the group comprising:

none/Q (1)
none/V (2)
none/Q (3)
none/L (4)
none/Q (5)
none/E (6)
L/V (12)
A/T (24)
S/P (45)
R/N (66)
K/V (80)
L/F (87)
R/S (92)
A/T (122)
V/L (123).

The mutation none/Q (1) means that an amino acid Q is added in position 1 (see FIG. 1 for the position of the amino acids).

In another embodiment of the invention, the modified and humanized anti-PA antibody according to the invention additionally comprises at least one mutation in the variable region of the light chain selected from the group comprising:

none/A (1)
none/I (2)
none/Q (3)
none/L (4)
Y/S (14)
K/R (18)
H/R (24)
Y/F (87)
S/P (96)
S/T (101)
L/V (124).

In a preferred embodiment of the invention, the modified and humanized anti-PA antibody according to the invention additionally comprises at least one mutation in the variable region of the heavy chain as described above and at least one mutation in the variable region of the light chain as described above. Preferably, the modified and humanized anti-PA antibody according to the invention additionally comprises the following mutations in the variable region of the heavy chain:

none/Q (1)
none/V (2)
none/Q (3)
none/L (4)
none/Q (5)
none/E (6)
A/T(122)
V/L (123), and the following mutations in the variable region of the light chain:

none/A (1)
none/I (2)
none/Q (3)

none/L (4)
L/V (124).

In a preferred embodiment of the invention, the modified and humanized anti-PA antibody according to the invention additionally comprises the following mutations in the variable region of the heavy chain:
none/Q (1)
none/V (2)
none/Q (3)
none/L (4)
none/Q (5)
none/E (6)
L/V (12)
A/T (24)
S/P (45)
R/N (66)
L/F (87)
R/S (92)
A/T (122)
V/L(123),
and the following mutations in the variable region of the light chain:
none/A (1)
none/I (2)
none/Q (3)
none/L (4)
Y/S (14)
K/R (18)
H/R (24)
Y/F (87)
S/P (96)
S/T (101)
L/V (124).

The invention relates to an anti-PA antibody modified according to the invention to increase its affinity and humanized according to the invention to increase its tolerance, in which the variable region of the heavy chain has the sequence SEQ ID NO: 15 and the variable region of the light chain has the sequence SEQ ID NO: 16.

The invention relates to an anti-PA antibody modified according to the invention to increase its affinity and humanized according to the invention to increase its tolerance, in which the variable region of the heavy chain has the sequence SEQ ID NO: 17 and the variable region of the light chain has the sequence SEQ ID NO: 18.

The invention relates to an anti-PA antibody modified according to the invention to increase its affinity and humanized according to the invention to increase its tolerance, in which the variable region of the heavy chain has the sequence SEQ ID NO: 19 and the variable region of the light chain has the sequence SEQ ID NO: 20.

The invention relates to an anti-PA antibody modified according to the invention to increase its affinity and humanized according to the invention to increase its tolerance, in which the variable region of the heavy chain has the sequence SEQ ID NO: 21 and the variable region of the light chain has the sequence SEQ ID NO: 22.

According to the above description of the amino acid sequences of the variable region of the heavy chain and of the variable region of the light chain of the anti-PA antibodies modified according to the invention, a person skilled in the art is capable of synthesizing, or causing to be synthesized, nucleic acids that code for these amino acid sequences.

The present invention therefore relates to a nucleic acid coding for a modified anti-PA antibody according to the invention, which has improved affinity relative to the nonmutated 35PA83 antibody, and which is or is not humanized.

The present invention also relates to a vector comprising said nucleic acid.

These nucleic acids can be comprised in a recombinant vector for cloning or for expression of the antibodies of the invention.

The present invention includes all the recombinant vectors containing coding sequences for eukaryotic or prokaryotic transformation, transfection or gene therapy. Said vectors can be prepared according to the conventional techniques of molecular biology and will additionally comprise a suitable promoter, optionally a signal sequence for export or secretion, and regulatory sequences necessary for the transcription of the nucleotide sequence.

A fusion polypeptide can be used for purifying the antibodies of the present invention. The fusion domain can for example include a polyhistidine tail, which permits purification on Ni+ columns, or a filamentous phage membrane anchor, which is particularly useful for gene library screening, according to the "phage display" technology.

A vector that is suitable within the scope of the invention is a recombinant DNA molecule adapted to receive and express a first and a second DNA sequence, so as to permit the expression of a heterodimeric antibody such as a full-length antibody or F(ab')2 or Fab fragments according to the invention. Such a vector supplies a system for independently cloning the two DNA sequences in two separate cassettes present in the vector, so as to form two separate cistrons for expression of a first and of a second polypeptide of the heterodimeric antibody. Said expression vector is called a di-cistronic vector.

The modified antibodies of the present invention can be produced in eukaryotic cells such as CHOs or human or murine hybridomas for example, as well as in plant cells.

The present invention also relates to prokaryotic or eukaryotic host cells, comprising a vector according to the invention.

Another object of the present invention is to supply a composition comprising at least one anti-PA antibody, modified according to the invention to improve its affinity, and optionally humanized.

The present invention also relates to a pharmaceutical composition comprising at least one anti-PA antibody modified according to the invention to improve its affinity, and optionally humanized.

Said pharmaceutical composition preferably comprises a pharmaceutically acceptable vehicle. Said vehicle corresponds in the sense of the invention to a nontoxic material that does not interfere with the effectiveness of the biological activity of the active ingredients of the composition. The term "pharmaceutically acceptable" refers to a nontoxic material that is compatible with a biological system such as a cell, a cell culture, a tissue or an organism. The characteristics of the vehicle will depend on the method of administration.

The present invention relates to the use of at least one anti-PA antibody modified to improve its affinity, and optionally humanized, according to the invention for the preparation of a pharmaceutical composition or of a medicinal product intended for the treatment or prevention of an infection with *Bacillus anthracis*.

The anti-PA antibody modified to improve its affinity, and optionally humanized, according to the invention can be labeled. Examples of markers comprise enzymes, radioisotopes, fluorescent compounds, colloidal metals, chemiluminescent compounds, and bioluminescent compounds. The methods of binding a marker to an antibody are well known by a person skilled in the art.

Another labeling technique consists of coupling the antibody to haptens of low molecular weight, and said haptens can be specifically modified by means of a second reaction.

Examples of haptens are biotin, which reacts with avidin, or dinitrophenol, pyridoxal or fluorescein, which can react with specific antihapten antibodies.

One object of the present invention is to supply a kit for the detection of an anthrax toxin comprising PA. This kit comprises:

a container comprising at least one anti-PA antibody modified according to the invention to improve its affinity, and optionally humanized, and which can be or labeled or not, optionally, a container comprising buffer solutions and optionally a container comprising means for detecting said labeled, modified anti-PA antibody, such as a biotin-binding protein, for example avidin or streptavidin, bound to a reporter molecule, such as a fluorescent or enzymatic marker. This container can also comprise means for detecting said nonlabeled, modified anti-PA antibody, i.e. essentially antibodies or antibody fragments.

The anti-PA antibody modified to improve its affinity, and optionally humanized, of the invention can be used in vitro, for example in immunological tests in which they are used in the liquid phase or bound to a vehicle of solid phase. Examples of vehicles that are well known are glass, polystyrene, polypropylene, polyethylene, dextran, nylon, amylase, natural or modified cellulose, polyacrylamide, agarose or magnetite. Examples of immunological tests using the anti-PA antibody of the invention are radioimmunoassays, histoimmunological labeling, ELISA, Western blots, immuno-precipitation assays, immunodiffusion assays, complement binding assays, FACS analyses or analyses using protein chips.

The object of the present invention is to supply a method of detection in vitro of an anthrax toxin, comprising PA, in a biological sample, comprising:

contacting the sample with at least one anti-PA antibody modified according to the invention to improve its affinity, and optionally humanized, and detecting the binding of said antibody as an indicator of the presence of said anthrax toxin.

The biological sample can be liquid: for example saliva, urine, cerebrospinal fluid, serum or blood, or solid or semi-solid, for example tissues or fecal matter or a solid tissue, as regularly used in histological diagnostics.

The present invention also relates to supplying a method of detection in vivo of an anthrax toxin comprising PA, in which an anti-PA antibody modified according to the invention to improve its affinity, optionally humanized, and labeled is administered to a subject. The amount of labeled modified antibody administered must be sufficient to permit detection of the binding of the antibody to the toxin. The amount of labeled modified antibody administered will depend on factors such as the subject's age and sex, as well as the stage of the disease. The amount administered can vary between 0.01 mg/kg and 50 mg/kg, preferably between 0.1 mg/kg and 20 mg/kg, and more preferably between 0.1 mg/kg and 2 mg/kg.

For carrying out the diagnosis in vivo, the modified anti-PA antibody of the invention must be bound to a radioisotope directly, or indirectly via functional groups. Functional groups commonly used are for example diethylenetriamine-pentaacetic acid (DTPA) and ethylenediaminetetraacetic acid (EDTA). Examples of radioisotopic metal ions are $^{111}$In, $^{97}$Ru, $^{67}$Ga, $^{68}$Ga, $^{72}$As, $^{89}$Zr and $^{201}$Tl.

The modified anti-PA antibody of the invention can also be labeled with a paramagnetic isotope for diagnosis by magnetic resonance imaging (MRI) or by electron spin resonance (ESR). Positron-emitting gamma radioisotopes can also be used, such as $^{157}$Gd, $^{55}$Mn, $^{162}$Dy, $^{68}$Ga, $^{52}$Cr, and $^{56}$Fe.

The anti-PA antibodies modified to improve their affinity, and optionally humanized, of the invention can also be used in vitro or in vivo for monitoring the development of the treatment of the disease, for example by determining the increase or the decrease in the number of cells targeted by anthrax toxins or the changes in the concentration of the PA toxin in a biological sample.

The present invention relates to a method of treatment of a subject, preferably a human, who may be infected by *Bacillus anthracis*, in which a therapeutically effective amount of an anti-PA antibody modified according to the invention to improve its affinity, and optionally humanized, is administered to said subject.

A therapeutically effective amount corresponds to an amount sufficient to reduce the symptoms of the disease and the development of the infection. This amount can vary with the subject's age and sex, and the stage of the disease and will be determined by a person skilled in the art. A therapeutically effective amount can vary between 0.01 mg/kg and 50 mg/kg, preferably between 0.1 mg/kg and 20 mg/kg, and more preferably between 0.1 mg/kg and 2 mg/kg, in one or more daily doses, for one or more days.

The method of administration can be by injection or by gradual infusion. Injection can be intravenous, intraperitoneal, intramuscular, subcutaneous or transdermal.

The preparations for parenteral administration can include aqueous or nonaqueous sterile solutions, suspensions or emulsions. Examples of nonaqueous solvents are propylene glycol, polyethylene glycol, vegetable oils, such as olive oil, or injectable organic esters such as ethyl oleate. Aqueous vehicles comprise water, alcohol/water solutions, emulsions or suspensions.

The present invention also relates to an immunoconjugate comprising an anti-PA antibody modified according to the invention to improve its affinity, optionally humanized, and bound, directly or indirectly, to a therapeutic agent.

These therapeutic agents comprise chemical agents, radionuclides, immunotherapeutic agents, cytokines, chemokines, toxins or enzyme inhibitors. Examples of toxins are the A-chain of diphtheria, the A-chain of exotoxin, the A-chain of ricin, the A-chain of abrin, the A-chain of modeccin, alpha-sarcin, *Aleurites fordii* proteins, dianthine proteins, *Phytolacca americana* proteins, momordica charantia inhibitor, curcin, crotin, sapaonaria officinalis inhibitor, gelonin, mitogellin, restrictocin, phenomycin, enomycin and tricothecenes. Examples of radionuclides are $^{212}$Bi, $^{131}$I, $^{131}$In, $^{91}$Y, and $^{186}$Re.

The present invention will be better understood from the additional description given below, which refers to examples of production of anti-PA antibody.

In the following examples, given for purposes of illustration, reference will be made to the appended drawings:

FIG. 1: string-of-pearls diagram of the variable region of the heavy chain and of the variable region of the light chain of the 35PA83 antibody.

The IMGT string-of-pearls representation is based on the IMGT numbering. The points indicate the differences between the human genes that are the most similar to 35PA83, and 35PA83. The shaded circles correspond to missing positions according to the IMGT numbering.

FIG. 2: sequence alignment between 3 modified anti-PA antibodies according to the invention (6.20, V2 and J24-7) and the parent antibody 35PA83

The positioning of the CDRs follows the definition of the IMGT (in light gray) or the definition of Kabat (in dark gray, Wu and Kabat 1970). The residues liable to mutation are in bold. All the residues are numbered according to the IMGT numbering.

MATERIALS AND METHODS

*E. coli* Strains

The following *E. coli* strains were used:

XL1 (Stratagene, La Jolla, Calif.): recA1, endA1, gyrA96 thi-1 hsdR17 sup E44 relA1 lac [F'proAB lacIqZΔM15 Tn10(Tetr)]

SURE (Stratagene): e14(McrA) Δ(mcrCB-hsdSMR-mrr) 171 endA1 supE44 thi-1 gyrA96 relA1 lac recB recJ sbcC umuC::Tn5 (Kanr) uvrC [F' proAB lacIqZΔM15 Tn10 (Tetr)]

HB2151, used for the expression of soluble Fabs.

Toxins

The anthrax toxins (PA83, LF and EF) were purchased from List laboratories.

Construction of the Library of 35PA83 Mutants

A library of mutant antibodies derived from the 35PA83 gene was generated by Massive Mutagenesis® (Biomethodes, Evry, France). The mutations were inserted in the CDRs of the heavy and light chains using NNS codons. The CDR regions were defined according to Kabat et al. (Wu and Kabat 1970) and IMGT (Lefranc, Pommie et al. 2003).

The DNA library was used for transforming the SURE cells by electroporation. After adding SB medium supplemented with carbenicillin to the culture and incubating for 1 h at 37° C., 1 ml of phage helper VCSM13 (about $10^{12}$ pfu) was added to the culture. After incubation for 2 h, 70 μg/ml of kanamycin was added and the culture was stirred overnight at 37° C.

Selection of Antibodies by Phage

The phage-Fab particles were purified and concentrated from 50 ml of culture by precipitation with PEG, then resuspended in 3 ml of 1% PBS-BSA—0.02% azide and filtered on a 0.45 μm filter. The titer of this preparation of phage was about 5 $10^{10}$ pfu/ml. The phages-Fab were submitted to three cycles of infection-selection-recovery as described previously (Andris-Widhopf, Rader et al. 2000). Certain phages were analyzed, or else submitted to one or other of the processes described below:

Selection by Elution at Very Low Concentration of Antigen

The library was screened using decreasing concentrations of biotinylated PA83 (100 nM, 10 nM, 1 nM, 0.1 nM, 0.01 nM, 0.001 nM) and magnetic beads covered with streptavidin μMACS (Milteny Biotech). Different mixtures of phages and of biotinylated antigen, at different concentrations, were incubated for 30 min at 37° C. in glass tubes. The phages bound to the biotinylated PA83 were captured using 100 μl of magnetic beads covered with streptavidin μMACS (5 min at room temperature). After capture of the phages, the beads were washed 5 times in PBS and once in TPBS (PBS containing 0.1% of Tween 20). The bound phages were then eluted by incubation with 100 μl of trypsin (10 μg/ml). The eluate was used for infecting the *E. coli* SURE bacteria in the exponential growth phase.

Selection by Long Incubation

Approximately $10^9$-$10^{10}$ phages per well (50 μl) were screened by binding to a plate (Nunc Maxisorp) covered with 5 μg/ml of PA83 in PBS and blocked with 5% of MPBS. The PA83 plate was incubated with the phages-Fab for 2 h at 37° C. and washed 5 times in 0.1% Tween 20-PBS and twice in PBS. The phages were then incubated at 4° C. with 50 μg/ml of soluble PA83 for specified times (1 day, 3, 13, 18, and 24 days). After 5 washings, the bound phages were eluted at 37° C. for 15 min with 50 μl of trypsin 10 μg/ml (Sigma) before reinfection of the *E. coli* SURE bacteria in the exponential phase.

Expression of Soluble Fab, Periplasmic Extraction and Purification

Each DNA variant was transformed in bacteria of the strain of *E. coli* called HB2151, which had been made chemically competent. The cells were cultivated at 30° C., stirred at 250 rpm in 1 L of SB medium containing 50 μg/ml of carbenicillin and 0.1% of glucose. When the culture reached an $A_{600}$ of 1.5, induction with 1 mM of IPTG was carried out for 18 h at 22° C.

The Fabs were extracted with polymyxin B sulfate (Sigma) and purified on a nickel column (Ni-NTA spin column, QIAGEN, Valencia, Calif.) according to the manufacturer's instructions, then dialyzed with PBS 1× at 4° C. for 3 h.

Quantification of the Soluble Fab

The purity of the Fab was tested by SDS-PAGE and its concentration was determined using the software Quantity One® (Biorad).

Real-Time Measurement of Surface Plasmon Resonance (SPR)

The kinetic constants of interaction between PA83 and the 35PA83 variants were determined using the system Biacore X SPR (BIAcore, Uppsala, Sweden). The PA83 was immobilized on a CM5-sensitive chip using a procedure for amine coupling by injection of 30 μl of 2 μg/ml of PA83 in 10 mM of sodium acetate pH 4.5. To minimize the probability of rebinding, $K_D$ was measured using a high flow rate (30 μl/min) and a minimum amount of coupled antigen (about 500 RU, resonance units). The degree of binding of different concentrations of Fab in the range from 5 to 400 nM in PBS was determined at a flow rate of 30 μl/min. The binding data were entered in a 1:1 Langmuir model of the BIA evaluation software. The association and dissociation constants ($k_{on}$ and $k_{off}$ respectively) for the binding of Fab to PA83 were determined at 35° C.

Sequence Analysis

The sequences of the heavy and light chains of the selected clones were determined by Genome Express (Meylan, France) using the primers ompseq and newpelseq (Andris-Widhopf, Rader et al., 2000). The sequences were analyzed in line, using the IMGT system (http:/imgt.cines.fr).

Test of Neutralization in vitro

The cell line of murine macrophage J774A.1 was incubated overnight at a density of 14 000 cells per well in 96-well plates. 400 ng/ml of PA and 40 ng/ml of LF were added simultaneously to the Fab or to the medium only and incubated for 1 hour at 37° C. The mixtures were then added to the macrophages and incubated for 4 h at 37° C. The Promega CytoTox 96 Assay Kit was then used according to the manufacturer's instructions to determine the $IC_{50}$ values of the Fab for LT neutralization (Pelat et al. 2007, Antimicrob. Agents Chemother 51, 2758-2764).

Results

Construction of the Fab Mutant Library (35PA83)

Affinity maturation in vitro was carried out to generate new variants displaying better affinity. For this purpose, a library of variants was generated by exclusive mutation of the residues of 6 CDRs, i.e. at positions. The size of the library is 5.4 $10^8$ transformants. 45 independent plasmid clones were sequenced to determine the diversity (Table 1) and the mutation rate. The experimental mutation rate is 3 mutations per fragment ($V_H$+$V_L$), which permits direct selection of the combinations of mutations that increase the affinity to PA.

Examination of the mutational frequency at each CDR position targeted in the nonselected library compared with the selected library (Table 1) showed that certain positions (in gray) are not tolerant to variation. Thus, the residues located at these positions seem to be key residues for binding to the antigen, preserving the integrity of the binding site to the antigen. In particular, the residues (H31-H40) of CDR1 are defined as antigen contact residues.

It appears that there was a substantial selection pressure during the selection process, as the nonselected library shows greater diversity in comparison with the selected sequences, in particular in L-CDR1 and H-CDR1.

Two positions (in black) are frequently mutated in the selected library: H117 and L27. With the exception of the mutant J24-15, the mutations of the serine residue H117 did not affect the antigen binding properties of the Fabs (Table 2). In contrast, the mutations of the residues Glutamine L27 seem unfavorable as they reduce the affinity of the Fab (mutant 6.7) or affect the efficiency of expression of the Fab (data not shown).

TABLE 1

Mutational frequencies at the CDR positions targeted

Fragment Fd

| H-CDR1 | G | D | S | I | S | G | G | Y | Y | W | S | | | | | |
|---|---|---|---|---|---|---|---|---|---|---|---|---|---|---|---|---|
| Mutational frequency % in the selected library | 0 | 5.5 | 1.8 | 0 | 0 | 3.7 | 0 | 0 | 0 | 0 | 0 | | | | | |
| Mutational frequency % in the nonselected library | 8.5 | 4 | 11 | 6 | 2 | 2 | 17 | 2 | 6 | 2 | 8 | | | | | |

| H-CDR2 | H | I | Y | G | S | T | A | D | T | R | Y | N | P | S | L | K | S |
|---|---|---|---|---|---|---|---|---|---|---|---|---|---|---|---|---|---|
| Mutational frequency % in the selected library | 1.8 | 0 | 0 | 0 | 0 | 0 | 0 | 0 | 0 | 11 | 3.7 | 3.7 | 3.7 | 1.8 | 0 | 1.8 | 0 |
| Mutational frequency % in the nonselected library | 4 | 2 | 0 | 4 | 0 | 0 | 0 | 4 | 0 | 17 | 4 | 15 | 2 | 15 | 6 | 4 | 8 |

| H-CDR3 | S | G | Y | N | F | W | S | G | E | Y | Y | G | L | D | S |
|---|---|---|---|---|---|---|---|---|---|---|---|---|---|---|---|
| Mutational frequency % in the selected library | 0 | 0 | 1.8 | 0 | 0 | 0 | 1.8 | 0 | 1.8 | 1.8 | 5.5 | 0 | 1.8 | 0 | 22 |
| Mutational frequency % in the nonselected library | 2 | 0 | 2 | 2 | 0 | 0 | 13 | 8 | 8 | 12 | 4 | 12 | 14 | 4 | 6 |

Light chain

| L-CDR1 | H | A | S | Q | G | I | N | S | W | L | A |
|---|---|---|---|---|---|---|---|---|---|---|---|
| Mutational frequency % in the selected library | 3.7 | 0 | 0 | 11 | 0 | 0 | 1.8 | 0 | 3.7 | 3.7 | 0 |
| Mutational frequency % in the nonselected library | 11 | 11 | 2 | 4 | 4 | 4 | 8 | 0 | 9 | 9 | 4 |

| L-CDR2 | K | A | S | S | L | Q | S |
|---|---|---|---|---|---|---|---|
| Mutational frequency % in the selected library | 5.3 | 0 | 3.7 | 5.5 | 11 | 14 | 15 |
| Mutational frequency % in the nonselected library | 6 | 0 | 8 | 13 | 6 | 12 | 10 |

TABLE 1-continued

| Mutational frequencies at the CDR positions targeted | | | | | | | |
|---|---|---|---|---|---|---|---|
| L-CDR3 | Q | Y | D | S | A | P | L | A |
| Mutational frequency % in the selected library | 0 | 0 | 1.8 | 0 | 7.4 | 3.7 | 1.8 | 3.7 |
| Mutational frequency % in the nonselected library | 0 | 4 | 2 | 0 | 6 | 4 | 19 | 17 |

Percentage of Sequences Mutated at a Given Position (54 Individual Sequences)

TABLE 2

| Affinity and kinetics of binding for Fab 35PA83 and its variants. | | | | |
|---|---|---|---|---|
| | sequence H | sequence L | $K_D$ (M) | $k_{on}$ ($M^{-1} \cdot s^{-1}$) | $k_{off}$ ($s^{-1}$) |
| Parent clone | | | | | |
| 35PA83 | parent | parent | $3.4 \; 10^{-9}$ | $9.3 \; 10^4$ | $3.2 \; 10^{-4}$ |
| Clones with clearly improved affinities | | | | | |
| v2 | G > S (31A) R > K (66) K > R (73) | parent | $6.6 \; 10^{-10}$ | $1.22 \; 10^5$ | $8.1 \; 10^{-5}$ |
| 6.20 | H > L (55) S > G (74) | Q > L (68) | $1.8 \; 10^{-10}$ | $2.86 \; 10^5$ | $5.1 \; 10^{-5}$ |
| J24-7 | parent | H > R (24) S > E (69) | $7.8 \; 10^{-10}$ | $4.35 \; 10^5$ | $3.4 \; 10^{-4}$ |
| J24-15 | S > L (117) | S > R (58) | $8.8 \; 10^{-10}$ | $3.41 \; 10^5$ | $3 \; 10^{-4}$ |
| Clones with degraded affinities | | | | | |
| v3 | parent | L > R (67) | $2.27 \; 10^{-8}$ | $8.98 \; 10^3$ | $2 \; 10^{-4}$ |
| 5.20 | parent | S > R (69) | $1.22 \; 10^{-8}$ | $2.4 \; 10^4$ | $2.91 \; 10^{-4}$ |
| 6.7 | parent | Q > V (27) S > L (66) | $8.11 \; 10^{-9}$ | $1.9 \; 10^4$ | $1.5 \; 10^{-4}$ |
| 6.40 | parent | H > R (24) | $1.10^{-8}$ | $1.9 \; 10^4$ | $2. \; 10^{-4}$ |
| Clones with affinities that are stable or little improved | | | | | |
| v8 | L > F (115) | A > S (117) | $2.54 \; 10^{-9}$ | $9.2 \; 10^4$ | $2.3 \; 10^{-4}$ |
| 3.5 | parent | Q > R (27) A > P (114) | $1.9 \; 10^{-9}$ | $0.8 \; 10^5$ | $1.5 \; 10^{-4}$ |
| 5.7 | S > R (29) S > R (117) | W > D (32) | $2.57 \; 10^{-9}$ | $5.5 \; 10^4$ | $1.4 \; 10^{-4}$ |
| 5.15 | S > A (117) | parent | $3.5 \; 10^{-5}$ | $8.85 \; 10^4$ | $3.11 \; 10^4$ |
| 5.47 | Y > T (112.4) | P > S (115) | $2.11 \; 10^{-9}$ | $8.81 \; 10^4$ | $1.86 \; 10^{-4}$ |
| 5.25 | parent | Q > R (68) | $2 \; 10^{-9}$ | $4.5 \; 10^4$ | $9 \; 10^{-5}$ |
| 5.39 | G > E (31A) D > G (28) | parent | $1.71 \; 10^{-9}$ | $0.63 \; 10^5$ | $1.08 \; 10^{-4}$ |
| 6.36 | Y > T (113) | P > S (115) | $2 \; 10^{-9}$ | $0.62 \; 10^4$ | $1.26 \; 10^{-5}$ |
| 6.2 | S > G (74) | A > G (114) | $2 \; 10^{-9}$ | $1.6 \; 10^5$ | $3.2 \; 10^{-4}$ |
| 6.46 | S > A (70) E > Q (112.3) S > R (117) | S > R (69) | $1.82 \; 10^{-9}$ | $6.9 \; 10^4$ | $1.26 \; 10^4$ |
| 6.49 | P > G (69) S > T (111.2) | parent | $1.55 \; 10^{-9}$ | $9.6 \; 10^4$ | $1.5 \; 10^{-4}$ |
| J24-3 | P > G (69) | parent | $1.5 \; 10^{-9}$ | $2 \; 10^5$ | $2.9 \; 10^{-4}$ |
| J24-12 | parent | A > D (114) | $3.5 \; 10^{-9}$ | $7.8 \; 10^4$ | $2.8 \; 10^{-4}$ |
| J24-13 | parent | D > E (108) | $1.5 \; 10^{-9}$ | $1.2 \; 10^5$ | $1.86 \; 10^{-4}$ |
| J24-14 | D > G (28) G > E (33) S > L (117) | parent | $3.3 \; 10^{-9}$ | $6.14 \; 10^5$ | $2.03 \; 10^{-4}$ |

The constants of association ($k_{on}$) and of dissociation ($k_{off}$) were determined by surface plasmon resonance (BIAcore) and $K_D$ was calculated as equal to the ratio $K_{off}/K_{on}$.

Screening of the Variants

The mutant library was submitted to 3 cycles (R1, R2 and R3) of infection-selection-recovery. After stage R3, 12 individual clones were analyzed by sequencing of $V_H$ and $V_L$. Among these 8 variants, 2 were found to be identical. 7 individual Fabs were therefore expressed as soluble Fabs. Three of them were expressed sufficiently to permit measurement of affinity by SPR.

| 12 sequences H + L | 4 parent | 34% | | |
|---|---|---|---|---|
| | 8 variants (2 identical) | 66% | 3 clones expressed 5 clones unexpressed | 37% 63% |

The triple mutant V2 showed a lower dissociation constant ($k_{off}$=8.1 $10^5$ s$^{-1}$) and a slightly faster association constant ($k_{on}$=1.22 $10^5$ M$^{-1}$·s$^{-1}$) than 35PA83, resulting in increase of affinity by a factor of 5.15. This mutant has 3 mutations in the variable domain of the heavy chain: one mutation (G31$_A$S) in H-CDR1 and two mutations in H-CDR2 (R66K, K73R).

After the third cycle, the phages were screened according to two additional selection processes: panning in wells covered with the antigen with long incubation ("selection by long incubation") or using soluble biotinylated antigen at very low concentration ("selection by elution at very low concentration of soluble antigen").

Selection by Elution at Very Low Concentration of Soluble Antigen

| Experiment | 1 | 2 | 3 | 4 | 5 | 6 | 7 | 8 | 9 |
|---|---|---|---|---|---|---|---|---|---|
| [biotinylated PA83] nM | 100 | 10 | 1 | 0.1 | 0.01 | 0.001 | 0.0001 | 0.00001 | 0 |
| phages eluted (×10$^3$) | 250 | 192 | 55 | 10 | 8.8 | 3.4 | 1 | 0.7 | 0.9 |

Library R3 was selected using decreasing concentrations of biotinylated PA83, in the range from 100 nM to 0.01 pM. 1 pM represents the lowest concentration permitting elution of more clones than the negative control. Individual clones, obtained on the basis of condition 6, were first analyzed by sequences of the heavy and light chains. About 35% of them had wild-type sequences.

Condition 6

| 43 sequences H + L | 15 parent | 35% | | |
|---|---|---|---|---|
| | 28 variants | 65% | Clones expressed Clones unexpressed | 47% 63% |

Among these 28 variants, 47% were sufficiently expressed to permit measurement of affinity by SPR. In view of the redundancy of the clones, 8 individual variants were expressed and their kinetic constants were measured. The antibody fragment possessing the best affinity constant ($K_D$=1.8 $10^{-10}$ M, i.e. an improvement by a factor of 18.9) is the triple mutant 6.20. This variant possesses two mutations in CDR2 of the heavy chain (H55L and S74G) and one mutation in CDR2 of the light chain (Q68L).

Selection by Long Incubation

| Incubation time (day) | 3 | 13 | 18 | 24 | 25 |
|---|---|---|---|---|---|
| phages eluted | 4000 | 5700 | 4000 | 18 | 0 |
| 14 sequences H + L | 3 parent 11 variants | 21% 78% | Clones expressed Clones unexpressed | 72% 27% | |

Of the 18 clones eluted on day 24, 14 were sequenced completely ($V_H$ and $V_L$) and only 3 were wild-type. 6 variants were sufficiently expressed to determine their kinetic constants. The double mutant J24-7 ($K_D$=7.8 $10^{-10}$ M) and J24-15 ($K_D$=8.8 $10^{-10}$ M) showed a binding affinity increased by a factor of 4.35 and 3.96 respectively.

Test of LT Neutralization in vitro

The 50% inhibitory concentration (IC$_{50}$) of the Fab parent 35PA83 is 5.6 nM.

The 50% inhibitory concentration was measured for the variants v2 and 6.20: IC$_{50}$ of Fab v2=0.9 nM and IC$_{50}$ of Fab 6.20=3.3 nM.

Variants v2 and 6.20 thus display better capacity for neutralization than the Fab parent 35PA83.

Humanization of the Variants

The antibodies injected in humans are very well tolerated when they are human. In contrast, the antibodies of animal origin can cause harmful side effects and are quickly eliminated. The hypervariable regions of the antibodies are, however, mutated to such an extent during affinity maturation that it is difficult, purely by analyzing their sequences, to define their origin. Since the Fabs do not have a constant region, the framework regions are the only regions involved in their tolerance.

To improve the tolerance of Fab 35PA83, and of the molecules that will be derived from it, this Fab was humanized. An automatic analysis was carried out on the IMGT server (http://imgt.cines.fr) and made it possible to localize, in the framework regions of Fab 35PA83, the residues different from those encoded by the human germline genes coding for the sequences closest to those of 35PA83. Syntheses or point mutations made it possible to obtain nucleotide sequences coding for variants of Fab 35PA83 and having one, or a small number of mutations increasing the homology with the human sequences. The mutations that did not cause significant degradation of affinity, relative to 35PA83, are shown in Tables 3 and 4. All of these mutations were linked to a new synthetic gene that codes for a Fab whose framework regions are 97.75% identical to the framework regions encoded by human germline genes, against 88.69% for the parent Fab, 35PA83. However, the affinity of this fully humanized variant ($K_D$=9 $10^{-9}$ M) is degraded by a factor of about 3 relative to Fab 35PA83.

TABLE 3 mutations of the framework regions of the heavy chain

| No. of the residue | 35PA83 | |
|---|---|---|
| 1 | none | Q |
| 2 | none | V |
| 3 | none | Q |
| 4 | none | L |
| 5 | none | Q |
| 6 | none | E |
| 12 | L | V |
| 24 | A | T |
| 45 | S | P |
| 66 | R | N |
| 80 | K | V |
| 87 | L | F |
| 92 | R | S |
| 122 | A | T |
| 123 | V | L |

TABLE 4 mutations of the framework regions of the light chain

| No. of the residue | 35PA83 | |
|---|---|---|
| 1 | none | A |
| 2 | none | I |
| 3 | none | Q |
| 4 | none | L |
| 14 | Y | S |
| 18 | K | R |
| 24 | H | R |
| 87 | Y | F |
| 96 | S | P |
| 101 | S | T |
| 124 | L | V |

In another study, the inventors attempted to determine which mutations in the framework regions of the heavy chain and of the light chain did not lead to changes in the affinity of Fab.

First, the mutations described in Tables 5 and 6 below were made in framework regions 1 and 4 of the heavy and light chain of 35PA83.

The variant obtained by these mutations is called Hu₁35PA83.

TABLE 5 mutations of the framework regions 1 and 4 of the heavy chain of 35PA83.

| No. of the residue | 35PA83 | |
|---|---|---|
| 1 | none | Q |
| 2 | none | V |
| 3 | none | Q |
| 4 | none | L |
| 5 | none | Q |
| 6 | none | E |
| 12 | L | V |
| 24 | A | T |
| 122 | A | T |
| 123 | V | L |

TABLE 5 mutations of the framework regions 1 and 4 of the light chain of 35PA83

| No. of the residue | 35PA83 | |
|---|---|---|
| 1 | none | A |
| 2 | none | I |
| 3 | none | Q |
| 4 | none | L |
| 14 | Y | S |
| 18 | K | R |
| 24 | H | R |
| 124 | L | V |

The dissociation constants Kd were measured by Bioacore for 35PA83 and the variant Hu₁35PA83. The results obtained are very similar: 3.40 nM for 35PA83 and 2.86 nM for Hu₁PA83.

Thus, the mutations made in framework regions 1 and 4 of the heavy chain and of the light chain of 35PA83 do not affect the affinity of 35PA83 for its antigen. Secondly, mutations were made in framework regions 2 and 3 of the heavy chain and of the light chain of 35PA83. These mutations are presented in Tables 6 and 7 below.

The variant obtained by the mutations described previously in framework regions 1 and 4 and by the mutations described below in framework regions 2 and 3 was called Hu₄PA83.

TABLE 6 mutations of framework regions 2 and 3 of the heavy chain of 35PA83

| No. of the residue | 35PA83 | |
|---|---|---|
| 45 | S | P |
| 66 | R | N |
| 87 | L | F |
| 92 | R | S |

TABLE 7 mutations of framework regions 2 and 3 of the light chain of 35PA83

| No. of the residue | 35PA83 | |
|---|---|---|
| 87 | Y | F |
| 96 | S | P |
| 101 | S | T |

The dissociation constants Kd were measured by Bioacore for 35PA83 and the variant Hu₄35PA83. The results obtained are very similar: 3.40 nM for 35PA83 and 3.72 nM for Hu₁PA83.

Thus, the mutations made in framework regions 1, 2, 3 and 4 of the heavy chain and of the light chain of 35PA83 as described in Tables 4 to 7 do not affect the affinity of 35PA83 for its antigen.

A neutralization test LT was also carried out according to the protocol described previously. The 50% inhibitory concentration measured for Hu₄35PA83 is 5.8 nM whereas that measured for 35PA83 is 5.6 nM.

Thus, the mutations made in framework regions 1, 2, 3 and 4 of the heavy chain and of the light chain of 35PA83 as described in Tables 4 to 7 do not affect the capacity for neutralization of 35PA83.

The invention claimed is:

1. A modified anti-protective antigen (PA) antibody comprising a variable heavy chain region comprising the sequence of SEQ ID NO: 15 and a variable light chain region comprising the sequence of SEQ ID NO: 16.

2. A modified anti-protective antigen (PA) antibody comprising a variable heavy chain region comprising the sequence of SEQ ID NO: 17 and a variable light chain region comprising the sequence of SEQ ID NO: 18.

3. A modified anti-protective antigen (PA) antibody comprising a variable heavy chain region comprising the sequence of SEQ ID NO: 19 and a variable light chain region comprising the sequence of SEQ ID NO: 20.

4. A modified anti-protective antigen (PA) antibody comprising a variable heavy chain region comprising the sequence of SEQ ID NO: 21 and a variable light chain region comprising the sequence of SEQ ID NO: 22.

5. A composition comprising at least one anti-PA antibody as claimed in any one of claims 1-4.

6. A pharmaceutical composition comprising at least one anti-PA antibody as claimed in any one of claims 1-4 and a pharmaceutically acceptable vehicle.

7. A kit for the detection of an anthrax toxin comprising PA, said kit comprising: a container comprising at least one labelled anti-PA antibody as claimed in any one of claims 1-4, and a container comprising means for detecting said labelled antibody.

8. An immunoconjugate comprising an anti-PA antibody as claimed in any one of claims 1-4 bound to a therapeutic agent.

* * * * *